(12) United States Patent
Comin et al.

(10) Patent No.: US 7,217,822 B2
(45) Date of Patent: May 15, 2007

(54) PROCESS FOR MAKING CABERGOLINE

(75) Inventors: Jorge Humberto Zenon Comin, Buenos Aires (AR); Gustavo Ariel Revelli, Buenos Aires (AR); Fernando Gabriel Bardi, Florida (AR)

(73) Assignee: Synthon IP Inc., Gainesville, VA (US)

( * ) Notice: Subject to any disclaimer, the term of this patent is extended or adjusted under 35 U.S.C. 154(b) by 0 days.

(21) Appl. No.: 11/377,397

(22) Filed: Mar. 17, 2006

(65) Prior Publication Data

US 2006/0287350 A1    Dec. 21, 2006

Related U.S. Application Data

(60) Provisional application No. 60/662,549, filed on Mar. 17, 2005.

(51) Int. Cl.
*C07D 457/04* (2006.01)
*C07D 457/02* (2006.01)

(52) U.S. Cl. .......................................... 546/14; 546/69

(58) Field of Classification Search .................. 546/14, 546/69
See application file for complete search history.

(56) References Cited

U.S. PATENT DOCUMENTS

| 4,526,892 A | 7/1985 | Salvati et al. |
| 5,382,669 A | 1/1995 | Candiani et al. |

FOREIGN PATENT DOCUMENTS

| GB | 2 074 566 A | 11/1981 |
| GB | 2 103 603 A | 2/1983 |
| WO | WO 93/18034 | 9/1993 |
| WO | WO 02/085902 A1 | 10/2002 |

OTHER PUBLICATIONS

Ashford et al. J. Org. Chem. 2002, 67, pp. 7147-7150.

*Primary Examiner*—Charanjit S. Aulakh
(74) *Attorney, Agent, or Firm*—Mark R. Buscher

(57) ABSTRACT

A process for making cabergoline uses silyl-protecting agents to protect the indole nitrogen atom.

16 Claims, No Drawings

PROCESS FOR MAKING CABERGOLINE

This application claims the benefit of priority under 35 U.S.C. § 119(e) from U.S. provisional application Ser. No. 60/662,549, filed Mar. 17, 2005, the entire contents of which are incorporated herein by reference.

BACKGROUND OF THE INVENTION

The present invention relates to a process for making the pharmaceutically active agent cabergoline and to intermediates useful in said process.

Cabergoline, chemically 1-[(6-allylergolin-8-β-yl)-carbonyl]-1-[3-(dimethylamino)-propyl]-3-ethylurea of the formula (1)

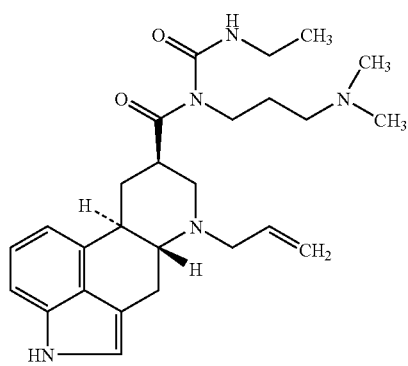

is a dopamine receptor agonist. It is a pharmaceutically useful compound that is indicated for the treatment of hyperprolactinemia and for the treatment of Parkinson disease. Cabergoline has been disclosed in GB 2074566 and U.S. Pat. No. 4,526,892.

A conventional process for making cabergoline was disclosed in GB 2103603 and comprises a reaction of the ergoline amide compound of formula (2) with ethyl isocyanate in an inert solvent (dioxane, benzene, toluene, cyclohexane).

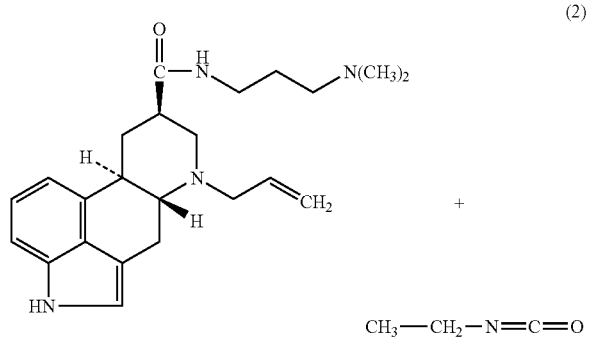

The process disclosed in GB 2103603 requires the use of a large excess of the isocyanate (up to 36 molar equivalents), high temperatures (70–120° C.) and long reaction times (24–72 hours). Despite these drastic conditions, the reaction results in equilibrium, i.e. the conversion is incomplete and is accompanied with serious side reactions on the indole nitrogen, which decreases the yield and complicates product purification.

The above process was improved in a later patent EPB 593692 (U.S. Pat. No. 5,382,669). The reaction of ethyl isocyanate with the compound (2) proceeds in the presence of a metal catalyst chosen from Ib and IIb metal group salts, preferably copper salts (CuCl, $CuCl_2$, CuBr and CuI) and of a phosphine of the formula $PR_6R_7R_8$ in which $R_6$, $R_7$ and $R_8$ are each, independently, an alkyl or aryl group optionally substituted by one or more substituents chosen from Cl, F, methyl and methoxy (preferably triphenylphosphine or tri-p-tolylphosphine) or of an alkyl phosphite, in a suitable solvent at a temperature 0–80° C., preferably 35–60° C. The amidic nitrogen is activated by the action of the copper catalyst. However the other nitrogen atoms, and particularly the indole nitrogen, may also be activated as well. The purpose of the phosphine/phosphite compound is to modulate the reaction, particularly to suppress the side reaction of the indole nitrogen atom. The large excess of the toxic and harmful ethyl isocyanate required by the earlier process may be decreased to 2–3 equivalents and the reaction proceeds in much milder conditions.

Despite this improvement, the process has serious drawbacks in low conversion rate (about 80%) and insufficient purity of the product; the latter being not much different from the uncatalyzed reaction (see the discussion in J. Org. Chem., 67, 7147 (2002)). The present inventors also confirm that the resulting cabergoline is contaminated with impurities and remainder of the starting material due to the incomplete conversion and low selectivity.

WO 2002/085902 relates to a further improvement of the production process. The amidic nitrogen of the starting ergoline-8.β-carboxamide (2) is first silylated by a silylation agent of general formula Y—Si ($R_6$)($R_7$)($R_8$), preferably with trimethylsilyl triflate, under presence of an organic amine. The so obtained silylated intermediate compound then reacts with the ethyl isocyanate without the need of any activating catalyst and finally the silylated cabergoline is deprotected:

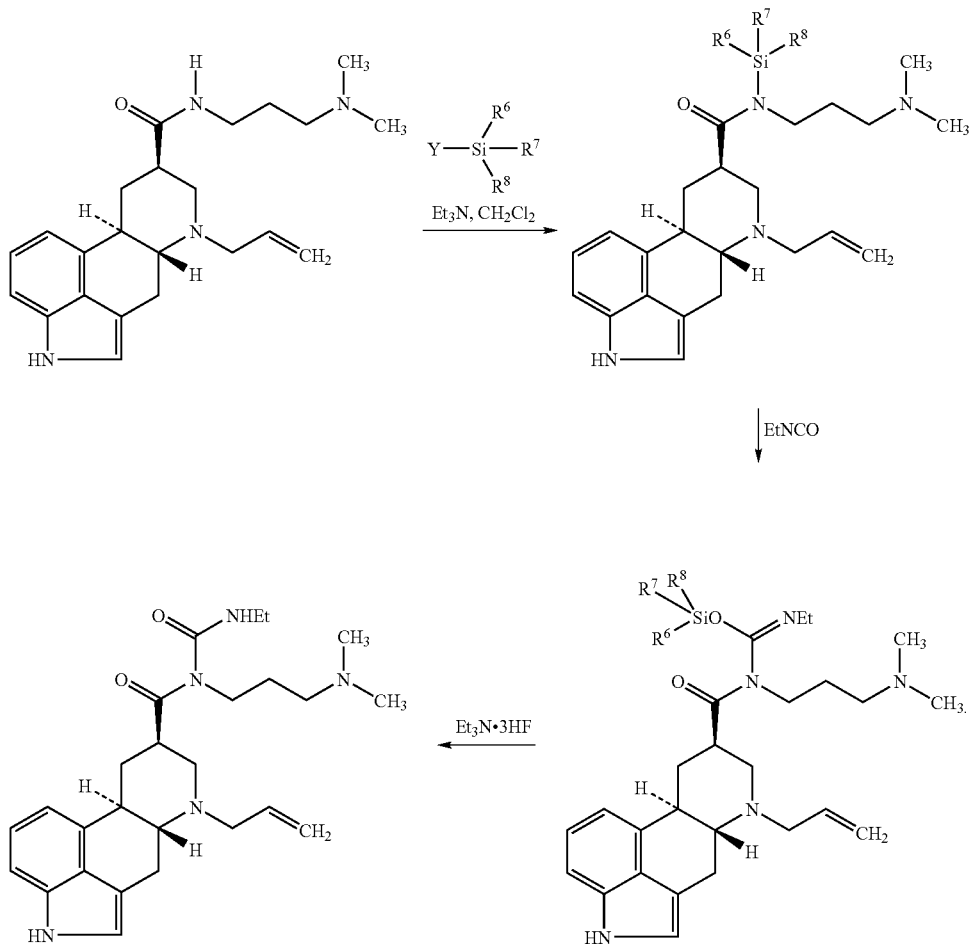

However, the cited document does not teach whether and/or how the silylated intermediates may be isolated and purified. Moreover, while the silylating agent activates the amidic nitrogen, it is not able to suppress the reactivity of the indole nitrogen. In fact, when repeating the process, the present inventors found that the silylated intermediate is very unstable (it is even not stable at ordinary conditions of TLC analysis, so that the reaction process cannot be monitored). Under disclosed conditions, the reaction was found incomplete and the product was accompanied with contaminants.

Ashford et al. (J. Org. Chem. 2002, 67, 7147–7150) studied the possibility of protecting the indole nitrogen in a variant process for making cabergoline. This scheme starts with the compound of formula (2), however it avoids the use of ethyl isocyanate. Instead, the compound (2), after its indole nitrogen has been protected by a tert.butoxycarbonyl group, reacts with phenylchloroformate to produce the compound (7)

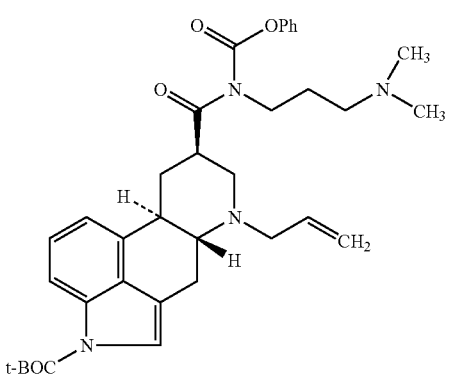

which is then converted into cabergoline by a reaction with ethyl amine, followed by deprotection. Ashford et al. also studied the possibility to protect the indole nitrogen in the compound (2) within the above process by a silylation agent, such as TMS or TIPS. However they found out that these protective groups are too unstable in the subsequent steps.

In conclusion, there is a need to develop an alternate and/or improved process for making cabergoline from the ergoline amide of formula (2), which process can have, inter alia, improved conversion and less potential for side reactions on the indole nitrogen.

SUMMARY OF THE INVENTION

Despite the fact that the prior art teaches away form the use of silylation agents for the indole nitrogen protection in cabergoline production, it has surprisingly been found that indole nitrogen protection by a silylation agent is a suitable and efficient tool for improving the "classical" synthetic process of cabergoline using ethyl isocyanate. Accordingly, a first aspect of the invention relates to a process, which comprises reacting in a solvent a compound of formula (2)

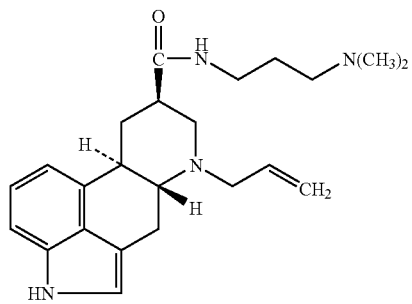
(2)

with a compound of the formula (4)

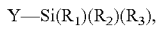
(4)

wherein $R_1$, $R_2$, and $R_3$ are each independently a C1–C6 alkyl group and Y represents a leaving group, such as a halogen or an alkyl- or arylsulfonyloxy group, in the presence of a strong base, typically an alkali metal hydride or alkali metal amide, to form a compound of formula (3)

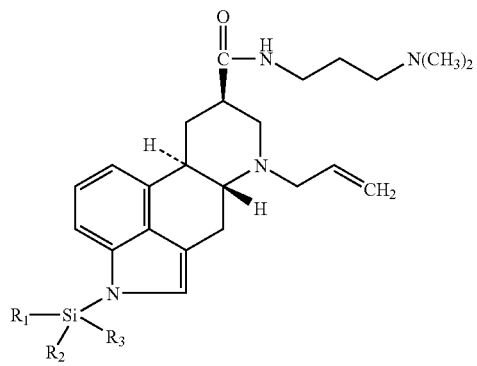
(3)

wherein $R_1$, $R_2$, and $R_3$ are each independently a C1–C6 alkyl group. In a preferred aspect, at least one of $R_1$, $R_2$, and $R_3$ is a branched C3–C6 alkyl group; most preferably, the $R_1$ and $R_2$ are methyl groups and the $R_3$ is a tert.butyl-group.

The process of conversion preferably comprises contacting, in a solvent, the compound of formula (2) with a strong base selected from an alkali metal hydride or alkali metal amide, followed by reaction of the formed anion (2a)

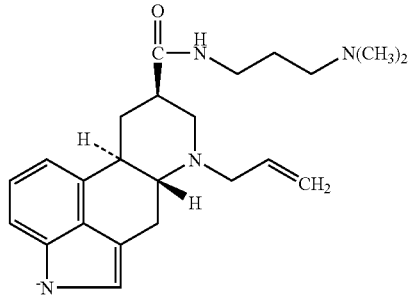
(2a)

with a compound of general formula (4)

$$Y-Si(R_1)(R_2)(R_3) \quad (4)$$

wherein Y is a leaving group, e.g. a halogen or alkyl- or arylsulfonyloxy group and $R_1, R_2, R_3$ are as above defined. A typical strong base is sodium hydride.

Another aspect of the invention relates to a process of making cabergoline of formula (1) comprising the step of conversion of the compound (3) into the compound (6)

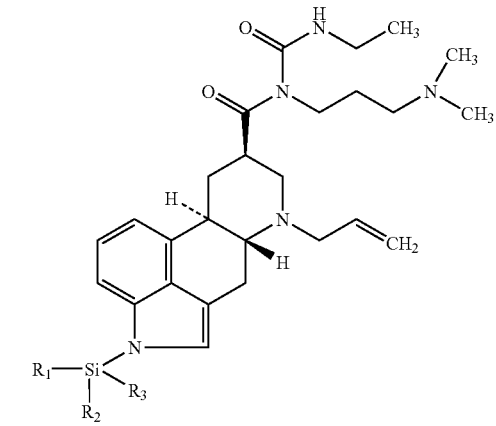
(6)

wherein $R_1, R_2, R_3$ are as above defined followed by deprotection to form cabergoline. Such conversion may be performed by the reaction of the compound of formula (3) with ethyl isocyanate in a solvent, in the presence of a copper (I) or copper (II) salt, preferably copper (I) halide. The deprotection step can be carried out by reacting the compound of formula (6) with ammonium fluoride or tetraalkylammonium fluoride.

A further aspect of the invention relates to compounds of the formulas (3) and (6).

By means of temporal protection of the indole nitrogen, the modified process for making cabergoline of the present invention does not require the huge excess of the ethyl isocyanate as in GB 2103603, nor a reaction modulator for suppressing the side reactions as in U.S. Pat. No. 5,382,669, is less sensitive to side reactions than WO 2002/085902 and it is one step shorter than the process of Ashford et al.

DETAILED DESCRIPTION OF THE INVENTION

The present invention deals in particular with a process for making cabergoline from an ergoline amide compound of formula (2). However, the basic indole silylation step is of basic and broad application in the synthesis of many structurally related compounds. The preparation of starting ergoline amide is described, for instance, in the Ashford et al.

In the first step of the process, the amide (2) is treated with a silylation agent in the presence of a strong base, which is able to convert the indole nitrogen into the corresponding anion (2a) shown above. Contrary to the procedure disclosed in WO 2002/085902, which employs the silylation agent in combination with an amine base, the silylation agent does not attack the amidic nitrogen within the process of this invention, but rather the formed indole nitrogen anion, which is more reactive. As a result, a silyl-protected compound of formula (3) is formed and the reactivity of the indole nitrogen for the next reaction(s) is suppressed.

In general, the useful silylation agent has the general formula (4),

$$Y\text{—}Si(R_1)(R_2)(R_3) \qquad (4)$$

in which the Y is a suitable leaving group, e.g. a halogen (preferably chlorine) or conventional alkyl- or arylsulfonyloxy group, and $R_1$, $R_2$, $R_3$ are the same or different and each of them independently represents a C1–C6 alkyl group. A preferred silylation agent is t-butyldimethylsilylchloride, trimethyl silyl chloride or triisopropyl silyl chloride.

Examples of the strong base are, for instance, Group Ia or IIa metal hydrides or amides, for instance sodium hydride or lithium diisopropylamide. An organometallic compound, such as butyl lithium, may also act as a strong base within the above definition, but it is less advantageous as it may cause side reactions on the amide carbonyl.

The reaction proceeds in an anhydrous inert aprotic solvent, which may be a hydrocarbon (such as hexane or cyclohexane), chlorinated hydrocarbon (such as dichloromethane), an cyclic ether (such as dioxane or tetrahydrofurane) and the like. In general, the reaction proceeds in an ambient or close to ambient temperature (from −20 to 50° C.), advantageously in an inert atmosphere. In practice, the compound (2) is preferably first mixed with the strong base to convert the indole nitrogen into an anion (the anion formation is generally indicated by a color change), and the silylation agent is added only afterwards to the so formed complex. After completion of the reaction (the progress of which may be monitored by common analytical methods), the rest of the unreacted strong base is decomposed (for instance with water). The reaction product of formula (3) can be separated from the metal salts arisen from the used base (for instance by extraction with an organic, water immiscible solvent) and isolated by common methods.

Various compounds of the general formula (3) may be isolated in solid state, properly characterized and, if necessary, purified. For instance, the particularly advantageous compound of the general formula (3) obtained by the reaction of compound of formula (2) with t-butyl dimethylsilylchloride—the "N-TBDMS-ergolineamide" (3a) may be isolated in solid state by crystallization of the reaction residue from the mixture of dimethylsulfoxide and water. Isolation of the compound (3) is however not generally required and the whole process leading to cabergoline may proceed within a "one-pot" procedure.

In a further step, the silylated compound of formula (3) can be converted into the corresponding silylated cabergoline derivative of formula (6). For such conversion, the compound of formula (3) generally reacts with ethyl isocyanate under presence of a copper (I) or copper (II) compound, for instance copper (I) chloride, in an organic solvent. The reaction generally proceeds at ambient temperature. Slight molar excess of ethyl isocyanate (3–5 fold) is recommended. No phosphine modulator is required. Contrary to the Ashford process, the silyl protective group remains attached.

The product (6) may be used for the next step basically without isolation. The rest of the copper catalyst should however be removed from the reaction mixture.

In the last step of the overall procedure, the N-silyl protective group is removed from the compound (6) by conventional methods, for instance by treating the compound of formula (6) with ammonium fluoride or tetrabutylammonium fluoride. Alternate deprotection methods known in the art may be used as well, however acidic conditions should be preferably avoided to prevent decomposition of cabergoline.

The so produced cabergoline may be finally isolated from the reaction mixture after removal the side products, particularly the fluorine and silicon-containing wastes, and preferably obtained in solid state, for instance by precipitation or crystallization from a suitable solvent, for instance from an etheral solvent such as methyl-tert.butyl ether.

In case of need or desire, cabergoline may be further purified, for instance by recrystallization, chromatography, extraction etc., as common in the art.

The invention will be further illustrated with reference to the following non-limiting examples.

EXAMPLE 1

Step 1 Compound of formula (3) [$R_1,R_2$=methyl, $R_3$=tert.butyl]

In a dry nitrogen atmosphere, a 100 ml flask is charged with 40 ml of anhydrous tetrahydrofuran and 0.75 g of a 60% sodium hydride dispersion in mineral oil. The suspension is stirred at room temperature for 10 minutes and 2.00 g of the ergoline amide compound of formula (2) is added. The suspension is stirred for 80 minutes at room temperature. A change in color is observed from beige to pink-orange. Then, 1.28 g of t-butyldimethylsilyl chloride is added. A change in color is observed giving a beige suspension. After stirring for 75 minutes at room temperature, the reaction mixture is quenched by addition of 2 ml of a 1:1 solution of tetrahydrofuran/water (hydrogen evolves). The resulting suspension is concentrated in a rotavapor and the residue is extracted with dichloromethane/water. The organic phase is dried over anhydrous sodium sulfate and concentrated in a rotavapor. The residue is eluted through a short silica gel 60 pad (dry column chromatography) to eliminate the mineral oil with a gradient from dichloromethane to dichloromethane/methanol 7% (saturated with ammonia). The fractions containing the product are concentrated in a rotavapor. To the residue, a mixture of 15 ml of dimethylsulfoxide and 3 ml water is added. The resulting suspension is heated to 85° C. giving a yellow solution. After cooling for 30 minutes in an ice bath, solids are collected by filtration and washed thoroughly with water. After drying under vacuum at 50° C., 2.24 g (86.5%) of the title compound is obtained.

Melting point 138–141° C., structure confirmed by 1H NMR.

Step 2 Compound of formula (6) [$R_1$,$R_2$=methyl, $R_3$=tert.butyl]

To a solution of the 2.24 g of the compound (3) [$R_1$, $R_2$=methyl, $R_3$=tert. butyl] in 22 ml of dry dichloromethane 0.54 g of copper (I) chloride is added. The suspension is stirred at room temperature for 5 minutes and then a solution of 2.25 ml of ethyl isocyanate in 22 ml of dry dichloromethane is slowly added by a dropping funnel in 30 minutes allowing gas interchange with the atmosphere. At the end of the addition, a dark brown suspension is formed. The suspension is stirred for another 30 minutes and partitioned with 200 ml of dichloromethane, 100 ml of water and 4.5 ml of concentrated ammonia. The organic phase is dried with anhydrous sodium sulfate and concentrated in a rotavapor, yielding the crude product (2.89 g)

Step 3 Cabergoline

The crude product from the preceded step (2.89 g) is dissolved in a solution of 45 ml of methanol and 7 ml of water. After addition of 2.46 g of ammonium fluoride the solution is stirred for 3 hours at room temperature. Concentration of the solution in a rotavapor affords a residue which is partitioned in 200 ml of dichloromethane, 100 ml of water and 2.25 ml of concentrated ammonia. The organic phase is dried with anhydrous sodium sulfate and concentrated in vacuo to give a yellow oil (2.09 g). The crude oil is dissolved in 8.4 ml of methyl t-butyl ether. The solution is seeded with cabergoline crystals and kept at −10° C. for 48 hours. After filtering, washing with cold methyl t-butyl ether and drying in vacuum at 45° C., 1.25 g of cabergoline was obtained.

EXAMPLE 2

In a dry nitrogen atmosphere, a 50 l flask is charged with 16 l of anhydrous tetrahydrofurane and 0.266 kg of a 60% sodium hydride dispersion in mineral oil. The suspension is stirred at room temperature and 0.800 kg of ergolineamide compound of formula (2) is added. The suspension is stirred at 40–45° C. for 1 hour. After cooling to 15–25° C., 685 g of trimethylsilyl chloride are added by a dropping funnel. The suspension is stirred at room temperature for 1 hour and then 264 g of copper (I) chloride are added. Nitrogen stream is disabled and by means of a dropping funnel, 898 g of ethyl isocyanate are added. The closed system is stirred for 1 hour and then the stoppers are removed allowing gas interchange with the atmosphere. After stirring 16 hours at room temperature, 0.8 l of a 1:1 tetrahydrofurane/water solution are added keeping temperature below 20° C. Additional 0.9 l of water is added. The deprotection step is performed adding 0.8 kg of ammonium fluoride and stirring for 2 hours at room temperature. The contents of the flask are transferred and concentrated at reduced pressure. The residue is partitioned between 18 l of dichloromethane, 10 l of water and 0.4 l of concentrated ammonia. The aqueous phase is re-extracted with dichloromethane (2×4 l) and the organic extracts combined. The combined organic extracts are washed with water and after treatment with activated charcoal the organic extract is filtered through a Celite pad. The filtrates are concentrated under reduced pressure and the residue extracted with n-heptane (2×2 l) to eliminate the mineral oil. The residue is crystallized three times from methyl-t-butyl ether to yield a first crop (473 g, mp: 96–98° C., HPLC purity: 99.8%). The combined mother liquors are concentrated under reduced pressure and purified by "dry column chromatography" (silica gel 60) employing a gradient dichloromethane/methanol 100:0 to 70:30. Selected combined fractions afford, after concentration, a residue that is crystallized from methyl-t-butyl ether to yield a second crop (119 g, mp: 96–98° C., HPLC purity: 99.9%). Total yield: 592 g.

Each of the patents, articles, and publications mentioned above is incorporated herein by reference in its entirety. The invention having been thus described, it will be obvious to the worker skilled in the art that the same may be varied in many ways without departing from the spirit of the invention and all such modifications are included within the scope of the present invention as set forth in the following claims.

What is claimed is:

1. A process, which comprises reacting in a solvent a compound of formula (2)

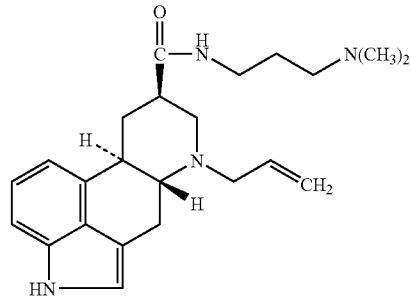

with a compound of the formula (4)

Y—Si($R_1$)($R_2$)($R_3$),  (4)

wherein $R_1$, $R_2$, and $R_3$ are each independently a C1–C6 alkyl group and Y represents a leaving group, in the presence of a strong base, to form a compound of formula (3)

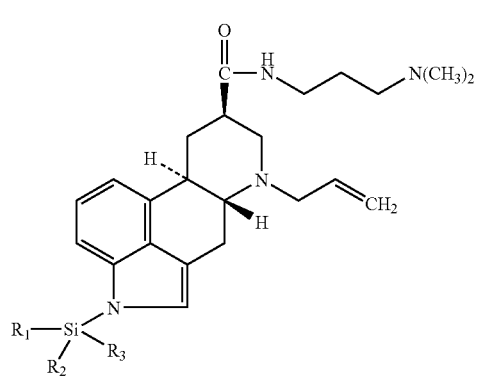

wherein $R_1$, $R_2$, and $R_3$ are each independently a C1–C6 alkyl group.

2. The process according to claim 1, wherein Y represents a halogen or an alkyl- or arylsulfonyloxy group.

3. The process according to claim 2, wherein Y represents chlorine.

4. The process according to claim 1, wherein said strong base is selected from an alkali metal hydride or alkali metal amide.

5. The process according to claim 4 wherein said strong base is sodium hydride.

6. The process according to claim 1, wherein $R_1$ and $R_2$ are methyl groups and $R_3$ is a tert.butyl-group or a methyl group.

7. The process according to claim 1, which further comprises: converting said compound of formula (3) into a compound of formula (6)

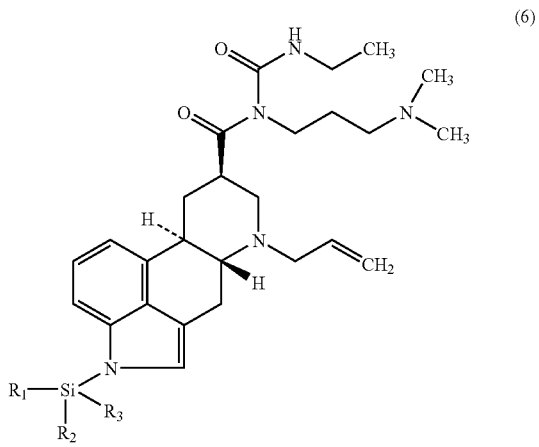

(6)

wherein $R_1$, $R_2$, and $R_3$ are as above defined; and deprotecting said compound of formula (6) to form cabergoline of formula (1):

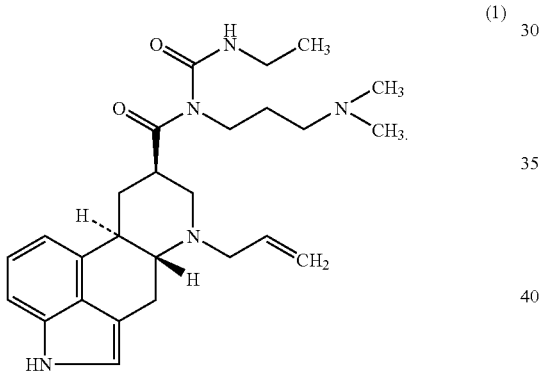

(1)

8. The process according to claim 7, wherein said conversion comprises reacting said compound of formula (3) with ethyl isocyanate in the presence of a copper (I) or copper (II) salt to form said compound of formula (6).

9. The process according to claim 8, wherein said copper salt is a copper (I) halide.

10. The process according to claim 8, wherein said strong base is sodium hydride.

11. The process according to claim 8, wherein Y represents a chlorine.

12. The process according to claim 8, wherein wherein $R_1$ and $R_2$ are methyl groups and $R_3$ is a tert.butyl-group or a methyl group.

13. The process according to claim 8, wherein said strong base is sodium hydride, Y represents a chlorine, $R_1$ and $R_2$ represent methyl groups, and $R_3$ represents a tert.butyl group.

14. The process according to claim 13, wherein said copper salt is a copper (I) halide.

15. A compound selected from the group consisting of formulas (3) and (6):

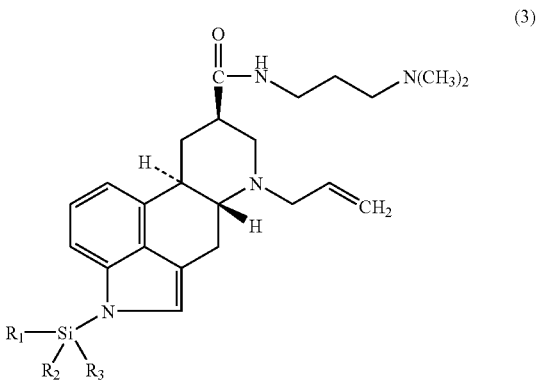

(3)

wherein $R_1$, $R_2$, and $R_3$ are the same or different and each of them independently represents a C1–C6 alkyl group;

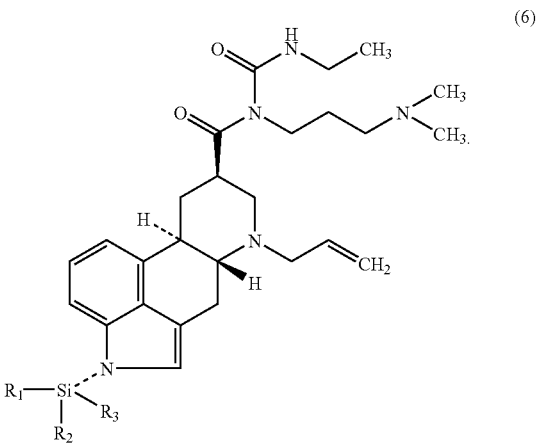

(6)

wherein $R_1$, $R_2$, and $R_3$ are the same or different and each of them independently represents a C1–C6 alkyl group.

16. The compound according to claim 15, wherein $R_1$ and $R_2$ are methyl groups and $R_3$ is a tert.butyl group.

* * * * *